United States Patent [19]

Mason, Jr. et al.

[11] 4,040,568
[45] Aug. 9, 1977

[54] DISPENSER FOR VAPORIZABLE MATERIAL ACCENTUATED BY AMBIENT AIR FLOW

[75] Inventors: Stanley I. Mason, Jr., Weston; Michael D. Handler, Bridgeport; James E. Richardson, Weston, all of Conn.

[73] Assignee: Simco, Inc., Weston, Conn.

[21] Appl. No.: 613,308

[22] Filed: Sept. 15, 1975

[51] Int. Cl.² ............................................. A61L 9/04
[52] U.S. Cl. ...................................... 239/57; 239/60
[58] Field of Search .................... 239/274, 54, 55, 56, 239/57, 60; 222/187

[56] References Cited

U.S. PATENT DOCUMENTS

| | | | |
|---|---|---|---|
| 2,578,827 | 12/1951 | Munnecke | 239/55 |
| 3,192,008 | 6/1965 | Dwyer | 239/274 X |
| 3,885,738 | 5/1975 | Chesmel et al. | 239/57 X |

Primary Examiner—Evon C. Blunk
Assistant Examiner—Michael Mar
Attorney, Agent, or Firm—Haynes N. Johnson

[57] ABSTRACT

A dispenser is provided for vaporizable materials such as deodorants and insecticides. The dispenser is adapted to create accentuated air flow over the materials either in the presence of ambient air flow or when the dispenser is moved through the air, for example, by being mounted on the back of a door. It dispenses far smaller quantities in the absence of air movement.

The dispenser includes one or more material containers open at one end and mounted within a vented housing. The vents on the housing are positioned over a portion of the open end of the contained material, and are recessed in a concave area of the housing. The housing is spaced from the material container and has exit ports along its periphery. The containers preferably have a dividing partition passing part way down the material container to provide paths for the air to flow down one side and up on the other for better contact with the vaporizable material. The result is that relative motion between the dispenser and the ambient air creates one-way air flow pattern into the central ports, across the vaporizable material, and out the back of the unit.

The unit is mounted in a place where it will periodically be moved, such as on a door, or where it would be subject to periodic air flows, such as on the wall adjacent a door.

12 Claims, 7 Drawing Figures

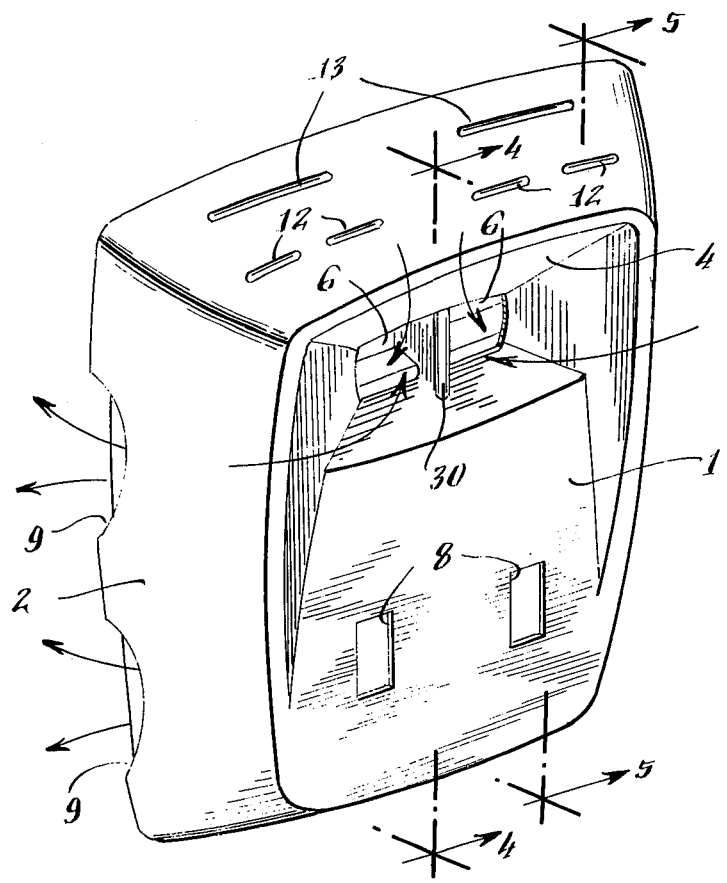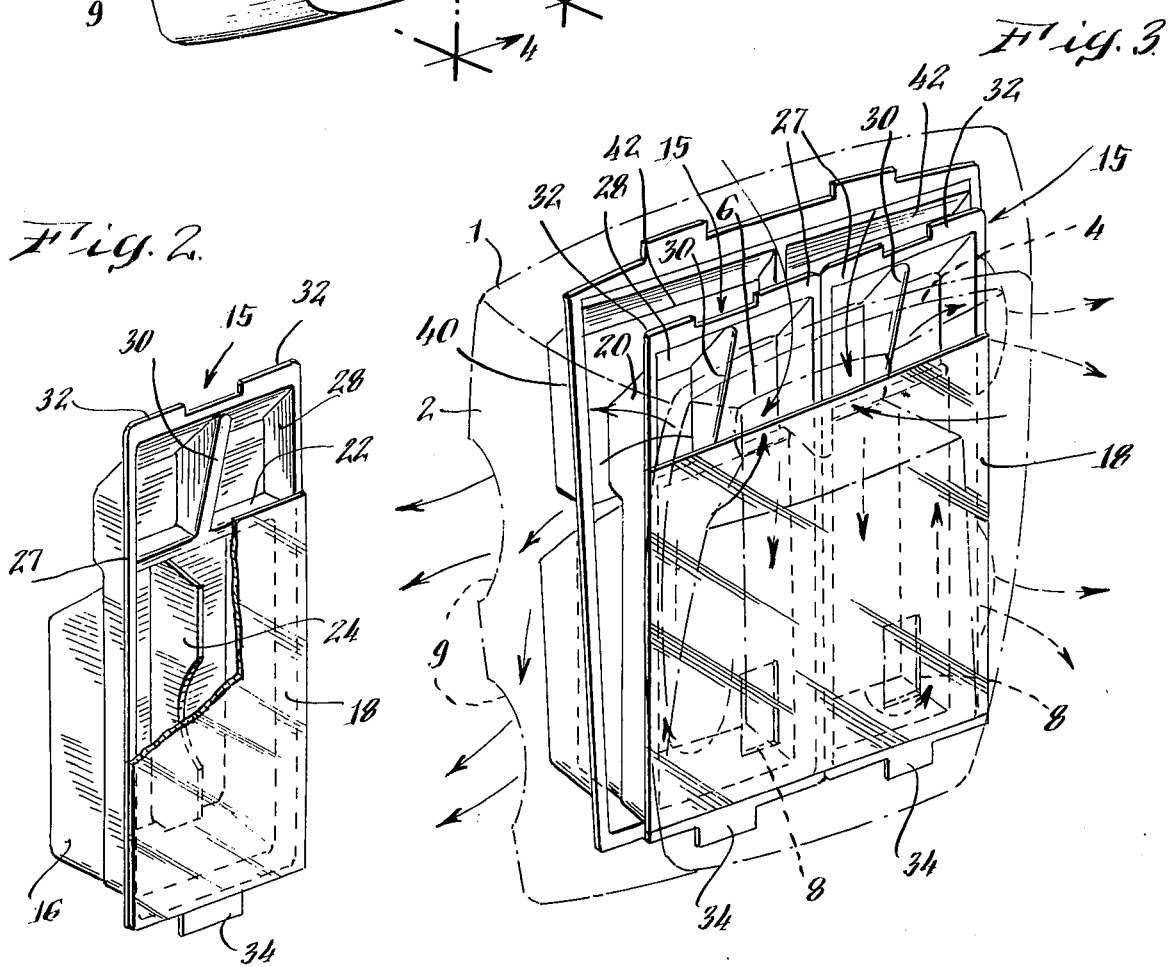

DISPENSER FOR VAPORIZABLE MATERIAL ACCENTUATED BY AMBIENT AIR FLOW

BACKGROUND OF THE INVENTION

Various dispensers exist for releasing material into the air, for air freshening, deodorizing, releasing insecticide material, and the like. Generally these allow the air to have access to the vaporizable material within but do not use periodic motion of the dispenser relative to the ambient air as a basis for generating additional dispensing of meaterial. Such "timed" dispensing is valuable, especially when the motion causing dispensing results from an activity wihtin the area that may, in itself, cause a need for additinal dispensing.

SUMMARY OF THE INVENTION

This invention involves a dispenser adapted to release desired volatile chemicals, such as air fresheners, insecticides and the like, into the air. It is particularly designed to release the material most efficiently in the presence of relative movement of ambient (surrounding) air.

The unit includes a container for the vaporisable material. The container is positioned vertically within a housing having air inlet and air outlet openings or ports. The air inlet ports are recessed within a concave portion of the housing. This tends to concentrate or accentuate the air in the inlet openings during ambient air motion and thus increase the velocity of the air into the openings. This would not occur in this manner in the absence of the concave recesses.

The material containers are open at one end and may have a partial partition running lengthwise from their openings. One side of the opening faces the air inlet port of the housing. Consequently, entering air passes through one side of the container opening, down into the container on one side of the partition, and out the container opening on the other side of the partition. Thus, the air flow pattern results in efficient contact between the air and the vaporizable material.

The enhanced air velocity through the inlet ports and over the vaporizable material thus tends more rapidly to mix the air with the material in the container to vaporize it. It also tends more efficiently to cause the air containing vaporizing material to go out the exit ports, possibly due to lowered internal pressure.

The unit is preferably mounted on a surface subject to periodic movement, such as the back of a door, or mounted adjacent to a moving surface, such as a door, so that an air flow is created into the recessed entry port whenever the door or a moving surface is in motion, or due to movement of persons nearby.

Description of the Drawings

FIG. 1 is a perspective view of the dispenser of the invention viewed generally from the front.

FIG. 2 is a perspective view of one of the material containers of a type used within the housing of the unit.

FIG. 3 is a phantom view of the unit used, showing direction of air flow within the dispenser occurring when the surrounding air is in motion.

DETAILED DESCRIPTION OF THE INVENTION

Figure 4:
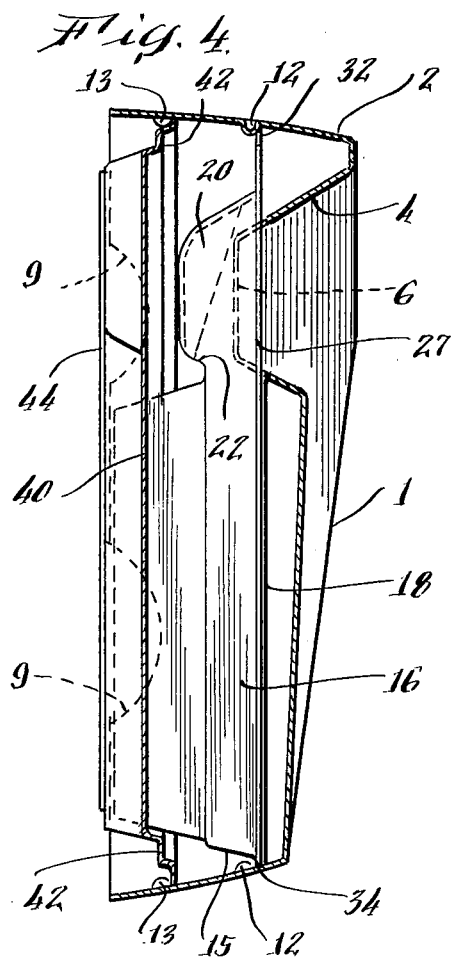
FIG. 4 is a cross-section taken vertically through the central portion of the dispenser (lines 4—4 of FIG. 1).

The dispenser of this invention, as seen by the user, is shown in FIG. 1 and is identified by the numeral 1. It includes a housing 2 having a concave recess 4 on the upper portion of the front of the unit. Air intake ports 6 are located at or near the innermost part of recess 4, i.e., the apex. If desired, additional inspection ports 8 may be located below ports 6 on the front of the housing. Ports 8 enable the user to be sure the unit contains adequate vaporizable material. The housing 2 has air outlet ports 9 along its back edge (or, in lieu of that, housing 2 may be mounted such that the back edge is slightly removed from the mounting surface).

Housing 2 also contains detents 12 and 13 at the top and bottom of the unit (bottom detents not shown). Detents 12 serve to receive and hold flanges from the inner container, and detents 13 are to receive flanges from the back face of the unit (described below).

Since the housing 2 is preferably made of lightweight plastic or other material, it can be flexed slightly so that the back face and the material container may be removed.

Figure 5:
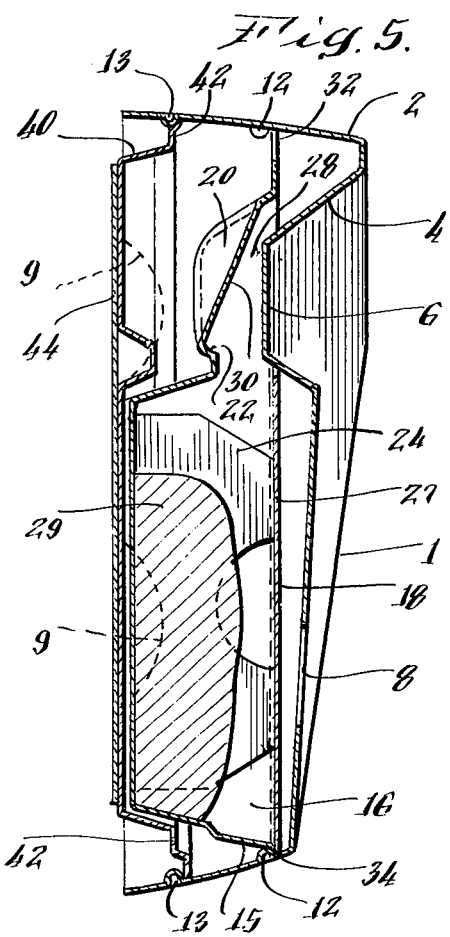
FIG. 5 is another vertical section taken through the dispenser, but across one of the recessed inlet ports (line 5—5 of FIG. 1).

FIG. 2 illustrates the material container 15 (a portion of its face has been removed to show the inside). Container 15 has a body portion 16, a transparent, flat front face 18, and an upwardly extending generally concave, cup-like extension 20. Container 15 has an opening 22 between the upper portion of body 16 and face 18, allowing access to material container 15. The access may be used to fill material container 15 (FIG. 5 shows vaporizable material 29 in container 15). More importantly, opening 22 serves to permit the entry of room air and to permit the exit of air mixed with vaporizable material. Preferably, container 15 is vertically mounted in housing 2 with opening 22 proximate to or at its upper portion.

Preferably, body 16 has a vertically extending air flow divider or partition 24. Partition 24 is mounted on the back surface of body 16 and contacts the inner surface of face 18. It does not extend all the say to the bottom of container 16 and has a cut out portion 25 midway down the partition and proximate to face 18. Though not always necessary, it is believed that use of the partition often gives more efficient air mixture control.

Body extension 20 has a concave shaped opening at the front, forming a port 28. Extension 20 may also include an air flow divider or partition 30 dividing port 28 into two sections, only one of which faces and is aligned with air intake port 6. Partition 30 should be aligned with partition 24.

As can be seen from the structure of container 15 and extension 20, air directed into one side of inlet port 28 will pass downwardly along one side of partition 30 and of partition 24 and (in the absence of any contained material) around the bottom of partition 24 and up the other side of the partition through the other side of port 28. With material present in the unit, the air flow would pass through opening 25 or, if more material were present, blocking that, across the top of partition 24 and below partition 30. Thus, the air flow itself is determined by the extent to which container 15 is holding vaporizing material. Often, due to the positioning of port 28 relative to port 6, a similar air flow pattern may be achieved in the absence of partition 24 and sometimes in the absence of partition 30 (see below).

The material containers 15 may be vacuumed formed of lightweight plastic material, the face 18 and the partition 24 being cemented in place. Partition 30 is preferably molded at the time of forming the unit. Two material containers 15, sometimes called blister packs, are used in each dispenser, one being positioned behind each of the openings 6.

Container 15 has two upwardly extending flanges 32 at the top and a downwardly extending flange 34 at the bottom. These fit within detents 12 of housing 2 in order to hold container 15 in position.

The dispenser is designed so that, when the container is in position, one of its ports 28 will be proximate to and aligned with inlet port 6, and the other of its ports 28 will not. The latter is positioned to discharge air within the housing 2 and thence through outlets 9.

Preferably, two containers 15 are used, positioned side by side. Each container uses one of the two inlet ports 6 in conjunction with container inlet port 28. The container may contain the same or different materials 28, as desired.

The dispenser unit, as previously mentioned, has a rear face 40 (FIGS. 4 and 5). Face 40 preferably has a waffle configuration so that it can be made of lightweight plastic and have adequate strength. It has flanges 42 extending upwardly and downwardly at its top and bottom ends so as to interconnect the back face with detents 13 in housing 2. The back surface of face 40 is covered with an adherent material 44, such as double face tape, so that the unit may be pressed against a smooth wall, door or other surface and will adhere.

Figure 6:
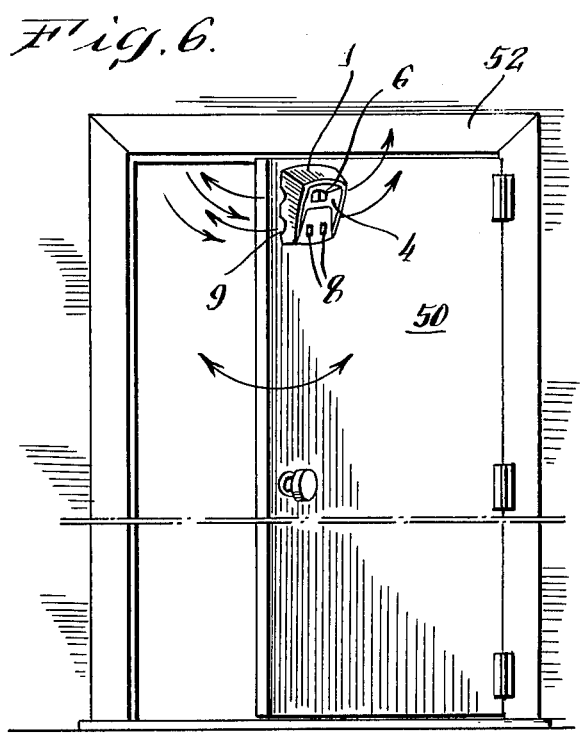
FIG. 6 is a view showing the unit mounted on a door which is partially open and in motion, showing how motion enhances the operation of the unit.
Figure 7:
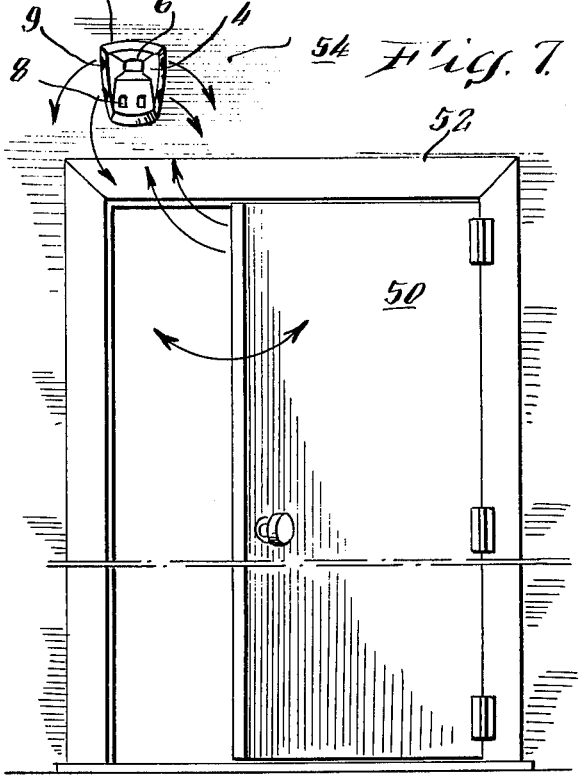
FIG. 7 is a picture of the unit mounted on a wall near a door which is in motion, once again showing how motion of ambient air helps to activate the unit.

FIGS. 6 and 7 show two typical methods of positioning dispenser 1. FIG. 6 shows the unit mounted on a door 50, so that concave recess 4 may receive air as the door is opened. FIG. 7 shows dispenser 1 mounted on wall 54 adjacent door 50 so that the recess 4 receives air flow as the door is being closed. These mountings are simply representative and show methods of positioning the dispenser so that there is relative motion between the surrounding ambient air and the dispenser for most efficient operation. It is also possible to have a base on the dispenser permitting it to be placed on a table or other surface near a source of occasional moving air.

OPERATION

The dispenser appears to operate due to air pressure differential between the front and back of the housing due to differences in the front and back configurations (when the surrounding air is in motion relative to the unit) and functions efficiently. Since the material container 15 is within a housing and so only partially open to the air, it dispenses relatively small quantities of material 29 (FIG. 5) from container 15 when the surrounding air is quiet. When, however, there is movement of the surrounding air, it dispenses relatively large quantities of material. Consequently, actions of persons in the room in which the unit is contained tend to cause it to dispense substantially more of the vaporizable material. This usually coincides with the times dispensing of the material is most needed and so provides more controlled dispensing.

For example, one set of tests has shown that my dispenser released only a third the amount of vaporizable material, while at rest, as compared to that released by a presently-available commercial dispenser, but released four times the amount in the presence of air motion. Thus, my unit dispensed twelve times as much in the presence of moving air as it did in still air. Though these ratios may vary with different conditions, they indicate the extent to which my dispenser serves volatile material when not needed and efficiently distributes it when it is, i.e., it dispenses relatively less under static air conditions and more efficiently in the presence of moving (dynamic) air.

Broadly speaking, air enters openings 6 at the apex of concave recess 4, circulates about the vaporizable material and carries away a portion of that material through outlet ports 9. Since the unit operates at a lower level in the absence of air motion, there is apt to be a high concentration of the material 29 in the air in container 15 immediately adjacent to the material so that initial actuation of air flow through the unit produces a highly concentrated flow of material from the dispenser.

As mentioned above, two containers 15 are positioned within housing 2. They are side by side with their ports 28 facing forwardly. Ports 28 are divided into two sections in each unit by partition 30 and the innermost portion only of the port 28 in each container 15 faces its respective port 6 in concave recess 4. Thus, the two units exist within the housing and operate in a mirror image fashion with respect to one another, and a description of the operation of one unit will suffice to describe both.

When the containers 15 are in position, the forward edge portion 27 of the respective extensions 20 (the inside edges) serve to divide the air intake port 6 into two separate ports.

As shown in the FIGS., and especially FIG. 3, air entering one of air intake ports 6 will pass through port 28 on body extension 20, on one side of the extension, will pass downwardly on that side through opening 22 and remain on one side of partition 24. It will then pass around the bottom of partition 24 or through opening 25, depending upon how much material 29 is within the unit and come upwardly on the other side of partition 24 and pass out through the other side of port 28, i.e., on the other side of partition 30. Since this portion of port 28 is not facing port 6 the air will not come out through port 6, but passes behind housing 2 over the front edge 27 of body extension 20 and thence out outlet ports 9. It will be noted in this respect that the depth and shape of recess 4 and its overall configuration must be such that edge portions 27 in the center of the unit can divide port 6 into two portions, but the inner surface of recess 4 will not contact forward edge 27 and its edge portion toward the outside of the unit. Thus, thence will be a gap between edge 27 and the inner surface of recess 4 adequate to permit passage of air through the gap and so to outlet port 9.

In the event the material 29 in the body 16 of container 15 substantially fills body 16, air flow will not go all the way down and back around partition 24. Rather, the air flow will be across partition 24 and will still have adequate and close contact with material 29. As material 29 is used and its level drops, then air will flow down partition 24 to the point where it can pass through opening 25 and return on the other side of the partition. As more material is vaporized, the air will, in due course, be able to go around at least part of the bottom portion of partition 24. Thus, the air flow pattern will vary depending upon the quantity of vaporizable material remaining in the unit and will compensate for the quantity of vaporizable material in the unit at any time.

It is possible, depending upon the configuration of the dispenser, to obtain a similar air flow pattern in the absence of partition 24. If so, partition 24 need not be included in container 15.

It has been found that the above air flow pattern is reversible, and the direction of motion depends upon the direction of motion of the impinging ambient air.

It can be seen that increased relative flow of surrounding air by such methods as are shown in FIGS. 6 and 7 will serve to increase the air flow within the unit, thus, enhancing dispensing of volatizable material from the unit.

In FIG. 6, dispenser 1 is mounted on the door. Opening of the door will cause an air flow pattern as described. Closing the door may cause air flow in the dispenser in the reverse direction; this also serves to dispense the volatile material. In FIG. 7, the dispenser is on the wall adjacent a door, so opening or closing the door will move the ambient air and actuate the unit. Such air motion can also be caused by movement of people in a room or hallway if the unit is located in a position near where people will pass.

When the material 29 in containers 15 is exhausted, the containers should be refilled or replaced. To do this, housing 2 is removed from the back face 44 by slightly flexing it so that detents 13 are released from flanges 42. This can be done without removing back face 40 from whatever surface it has been adhered to by adherent material 44. Similarly, by further flexing housing 22, flanges 32 and 34 can be separated from detents 12 and material containers 15 removed. They may then be refilled through opening 22 or replaced with new material containers. The container is then inserted into housing 2 by the reverse of the above process, and housing 2 secured similarly to back face 40.

We claim:

1. A dispenser for releasing volatile material in the presence of surrounding air movement, said dispenser including,
   a pair of similar containers, each containing volatile material, said containers each having an opening at one end thereof and a partitioned container extension proximate to said opening, said extension being concave towards said opening,
   a housing having an air inlet on one surface thereof and an air exit,
   means for mounting said containers in said housing with part of each said extension facing and opening to said air inlet, and so the remaining portion of said extension facing the inside surface of said housing and defining a gap therebetween,
   whereby ambient air may enter one side of each said container extension, pass into said container and leave, carrying volatile material, out the other side of said container extension.

2. A dispenser as claimed in claim 1 in which said air inlet is in a recessed portion of said housing.

3. A dispenser as claimed in claim 1 including a partition in said container, said partition being aligned with the partition in said container extension.

4. A dispenser for dispensing volatile material, such as deodorant or insecticide, adapted to release relatively small amounts of said material in the absence of ambient air movement and relatively large amounts when there is ambient air movement, said dispenser including
   a housing having an air inlet port and an air exit,
   a volatile material container having an air access opening, said container being mounted vertically with said air access opening proximate to the top thereof,
   said container being mounted within said housing with a portion of its air access opening facing said air inlet port and with the remainder of said opening positioned to permit air flow between said remainder and said air exit, and
   said air access opening having a cup-like configuration and including a vertical partition therein separating the said portion facing said air inlet port from said remainder of said opening,
   whereby ambient air movement will cause air flow into said container to remove and dispense volatile material.

5. A dispenser as claimed in claim 4 in which said container includes a partition therein aligned with said first-named partition.

6. A dispenser for dispensing volatile material, such as deodorant or insecticide, adapted to release relatively small amounts of said material in the absence of ambient air movement and relatively large amounts when there is ambient air movement, said dispenser including
   a housing having an air inlet port and an air exit,
   two volatile material containers having an air access opening, said containers being positioned side-by-side within said housing,
   said containers being mounted within said housing with a portion of their air access openings facing said air inlet port and with the remainder of said openings positioned to permit air flow between said remainder and said air exit and with the inner edges of said containers dividing said air inlet port into two ports.

7. A dispenser as claimed in claim 6 in which said container is partitioned to provide for air flow in opposite directions within said container when said dispenser is in the presence of ambient air flow.

8. A pair of containers for use in a dispenser, said dispenser including a housing with an air inlet on one face thereof and an air exit, said containers each including
   a container body, volatile material in said body,
   an opening in said container proximate one end thereof,
   a container body extension formed at one end of said body proximate said opening, said extension being curved to direct air flow to and away from said opening,
   means for mounting said body within said housing with at least a portion of said extension facing the air inlet in said housing, and
   said containers being joined along one edge thereof with their respective container body extensions adjacent each other, whereby portions of both said extensions face said air inlet.

9. A dispenser for dispensing volatile material, such as deodorant or insecticide, adapted to release relatively small amounts of said material in the absence of ambient air movement and relatively large amounts when there is ambient air movement, said dispenser including
   a housing having a fixed concave air inlet port and an air exit, a volatile material container having an air access opening, said container being mounted within said housing with a portion of its air access opening facing said air inlet port and with the remainder of said opening positioned to permit air flow between said remainder and said air exit, whereby ambient air movement will cause air flow into said container to remove and dispense volatile material, and said container being partitioned to provide for air flow in opposite directions within said container when said dispenser is in the presence of ambient air flow.

10. A dispenser for releasing volatile material in the presence of surrounding air movement, said dispenser including, a container containing volatile material, said container having an opening at one end thereof and a partitioned container extension proximate to said opening, said extension being concave towards said opening, a housing having an air inlet on one surface thereof and an air exit, means for mounting said container in said housing with part of said extension facing and opening to said air inlet with the remaining portion of said extension facing the inside surface of said housing and defining a gap therebetween, whereby ambient air may enter one side of said container extension, pass into said container and leave, carrying volatile material, out the other side of said container extension.

11. A dispenser for dispensing volatile material, such as deodorant or insecticide, adapted to release relatively small amounts of said material in the absence of ambient air movement and relatively large amounts when there is ambient air movement, said dispenser including a housing having an air inlet port and an air exit, a volatile material container having an air access opening, said container being mounted vertically with said air access opening proximate to the top thereof, said container being mounted within said housing with a portion of its air access opening facing said air inlet port and with the remainder of said opening positioned to permit air flow between said remainder and said air exit, and said air access opening having a cup-like configuration and including a means therein separating the said portion facing said air inlet port from said remainder of said opening, whereby ambient air movement will cause air flow into said container to remove and dispense volatile material.

12. A dispenser as set forth in claim 10 in which said container includes a partition therein aligned with said means separating the said portion facing said air inlet port from said remainder of said opening.

* * * * *